United States Patent
Hyogo et al.

(10) Patent No.: US 9,433,361 B2
(45) Date of Patent: Sep. 6, 2016

(54) BIOLOGICAL INFORMATION MONITOR

(75) Inventors: Mitsushi Hyogo, Tokyo (JP); Teiji Ukawa, Tokyo (JP); Yoshihiro Sugo, Tokyo (JP); Hiroko Hagiwara, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 425 days.

(21) Appl. No.: 12/872,099

(22) Filed: Aug. 31, 2010

(65) Prior Publication Data

US 2011/0054328 A1 Mar. 3, 2011

(30) Foreign Application Priority Data

Aug. 31, 2009 (JP) ................... 2009-199961

(51) Int. Cl.
  *A61B 5/02* (2006.01)
  *A61B 5/0225* (2006.01)
  *A61B 5/021* (2006.01)
  *A61B 5/022* (2006.01)

(52) U.S. Cl.
  CPC ......... *A61B 5/0225* (2013.01); *A61B 5/02125* (2013.01); *A61B 5/02225* (2013.01)

(58) Field of Classification Search
  CPC .. A61B 5/02154; A61B 5/021; A61B 5/441; A61B 5/0205; A61B 5/0215; A61B 5/02152; A61B 5/02216; A61B 5/022; A61B 5/02208; A61B 5/02225; A61B 5/023; A61B 5/0235; A61B 5/023233; A61B 5/024; A61B 5/02438; A61B 5/026; A61B 5/028; A61B 5/0535
  USPC ....................................................... 600/485
  See application file for complete search history.

(56) References Cited

U.S. PATENT DOCUMENTS 5,752,920 A 5/1998 Ogura et al.
5,876,348 A 3/1999 Sugo et al.
(Continued)

FOREIGN PATENT DOCUMENTS

| CN | 1868399 A | 11/2006 |
|---|---|---|
| JP | 11-31888 A | 2/1999 |
| JP | 2000-107146 A | 4/2000 |
| JP | 3054084 B2 | 4/2000 |

OTHER PUBLICATIONS

Extended European search report dated Nov. 10, 2010 issued in corresponding European application No. 10174592.5 ; 6 pages.
(Continued)

*Primary Examiner* — Patricia Mallari
*Assistant Examiner* — Vasuda Ramachandran
(74) *Attorney, Agent, or Firm* — Sughrue Mion, PLLC

(57) ABSTRACT

A biological information monitor includes: a first measuring unit which measures a pulse wave propagation time of a patient; a second measuring unit which measures a blood pressure of the patient; a calculating unit which calculates an estimated blood pressure value of the patient based on the pulse wave propagation time of the patient; a setting unit which sets a threshold; and a determining unit which compares the estimated blood pressure value with the threshold. The second measuring unit is activated to measure the blood pressure of the patient at least one of at time intervals and at a time when an operator operates the second measuring unit, and the second measuring unit is activated to measure the blood pressure of the patient by the determining unit based on the comparison result.

5 Claims, 6 Drawing Sheets

(56) References Cited

U.S. PATENT DOCUMENTS

| | | | |
|---|---|---|---|
| 6,007,358 | A | 12/1999 | Nagase |
| 6,196,974 | B1 | 3/2001 | Miwa |
| 6,527,725 | B1* | 3/2003 | Inukai et al. ............ 600/485 |
| 2004/0019284 | A1 | 1/2004 | Kawaguchi et al. |
| 2007/0016086 | A1 | 1/2007 | Inukai et al. |
| 2008/0033310 | A1* | 2/2008 | Yu et al. ............ 600/493 |

OTHER PUBLICATIONS

Office Action, dated Oct. 29, 2012, issued by the State Intellectual Property Office of the People's Republic of China in counterpart Chinese Patent Application No. 201010272049.4.

Office Action dated Jan. 21, 2013 issued by the Japanese Patent Office in counterpart Japanese Application No. 2009-199961.

* cited by examiner

SET EXAMPLE 1

SET EXAMPLE 2

SET EXAMPLE 3

BIOLOGICAL INFORMATION MONITOR

BACKGROUND OF THE INVENTION

The present invention relates to a biological information monitor in which a pulse wave propagation time (PWTT) measuring unit and a noninvasive blood pressure (NIBP) measuring unit are used together.

Japanese Patent No. 3,054,084 discloses a related art of a blood pressure monitor apparatus in which a pulse wave propagation time measuring unit and a noninvasive blood pressure measuring unit are used together.

Japanese Patent No. 3,054,084 discloses the following configuration.

Referring to FIG. 3, a blood pressure monitor apparatus 8 includes: a cuff 10 which has a belt-like cloth bag and a rubber bag accommodated in the cloth bag, and which is attached to be wound around, for example, an upper arm 12 of a patient; a pressure sensor 14; a selector valve 16; and an air pump 18. The pressure sensor 14, the selector valve 16, and the air pump 18 are connected to the cuff 10 via a piping 20. The selector valve 16 is configured so as to be selectively switched to one of three states: an inflation state in which pressurized air is allowed to be supplied to the cuff 10; a slow-deflation state in which the pressurized air in the cuff 10 is slowly discharged; and a quick-deflation state in which the pressurized air in the cuff 10 is quickly discharged.

The pressure sensor 14 detects the pressure in the cuff 10, and supplies a pressure signal SP indicative of the detected pressure to each of a static pressure filter circuit 22 and a pulse wave filter circuit 24. The static pressure filter circuit 22 includes a low-pass filter, extracts a static component contained in the pressure signal SP, i.e., a cuff pressure signal SK indicative of the cuff pressure, and supplies the cuff pressure signal SK to an electronic control device 28 via an A/D converter 26. The pulse wave filter circuit 24 includes a band-pass filter, extracts, on a frequency base, a pulse wave signal $SM_1$ which is an oscillating component of the pressure signal SP, and supplies the pulse wave signal $SM_1$ to the electronic control device 28 via an A/D converter 30. The pulse wave signal $SM_1$ represents the cuff pulse wave which is an oscillatory pressure wave that is produced from a brachial artery (not shown) in synchronism with the heartbeat of the patient, and that is then transmitted to the cuff 10.

The electronic control device 28 is configured by a so-called microcomputer including a CPU 29, a ROM 31, a RAM 33, an I/O port (not shown), and the like. The CPU 29 processes signals according to control programs pre-stored in the ROM 31 by utilizing the storage function of the RAM 33, and supplies drive signals through the I/O port to control the selector valve 16 and the air pump 18.

An electrocardiograph 34 continuously detects an electrocardiogram indicative of the action potential of the cardiac muscle through a plurality of electrodes 36 which are applied to predetermined portions of a living body, and supplies a signal $SM_2$ indicative of the electrocardiogram to the electronic control device 28. The electrocardiograph 34 is used for detecting a Q-wave or R-wave of the electrocardiogram which corresponds to a timing when the pumping output of blood from the heart toward the aorta is started.

A photoplethysmogram detecting probe 38 (hereinafter, referred to simply as the "probe") for a pulse oximeter detects a pulse wave propagated to a peripheral artery including capillaries. For example, the probe is attached to the skin of the living body or the body surface 40 such as a finger tip of the subject in a closely contacted state by a harness (not shown). The probe 38 includes: a container-like housing 42 which opens in one direction; a plurality of first and second light emitting elements 44a, 44b (hereinafter, referred to simply as the light emitting elements 44 in the case where they need not be discriminated from each other) each of which is configured by an LED or the like, and which are disposed on an outer peripheral portion of an inner bottom surface of the housing 42; a light receiving element 46 which is configured by a photodiode, a phototransistor, or the like, and which is disposed on a middle portion of the inner bottom surface of the housing 42; a transparent resin 48 which is integrally disposed in the housing 42 to cover the light emitting elements 44 and the light receiving element 46; and annular shade members 50 which are disposed between the light emitting elements 44 and the light receiving element 46 in the housing 42, for preventing light emitted toward the body surface 40 by the light emitting elements 44 and reflected from the body surface 40, from being received by the light receiving element 46.

For example, the first light emitting element 44a emits red light having a wavelength of about 660 nm, and the second light emitting element 44b emits infrared light having a wavelength of about 800 nm. The first and second light emitting elements 44a, 44b alternately emit the red light and the infrared light for a predetermined time period at a predetermined frequency. The light emitted toward the body surface 40 by the light emitting elements 44 is reflected from a body portion where capillaries densely exist, and the reflected light is received by the common light receiving element 46. The wavelengths of the light emitted from the light emitting elements 44 are not restricted to those described above as far as the first light emitting element 44a emits light having a wavelength which exhibits significantly different absorption factors with respect to oxygenated hemoglobin and reduced hemoglobin, and the second light emitting element 44b emits light having a wavelength which exhibits a substantially same absorption factors with respect to the two kinds of hemoglobin, or namely emit light having a wavelength which is reflected by oxygenated hemoglobin and reduced hemoglobin.

The light receiving element 46 outputs a photoplethysmogram signal $SM_3$ the level of which corresponds to the amount of the received light, through a low-pass filter 52. An amplifier and the like are adequately connected between the light receiving element 46 and the low-pass filter 52. The low-pass filter 52 eliminates noises having a frequency higher than that of the pulse wave, from the photoplethysmogram signal $SM_3$ input thereto, and outputs the resulting signal $SM_3$ from which the noises are eliminated, to a demultiplexer 54. The photoplethysmogram indicated by the photoplethysmogram signal $SM_3$ is a volume pulse wave which is generated in synchronism with the pulse of the patient. The photoplethysmogram corresponds to a pulse-synchronous wave.

The demultiplexer 54 is alternately switched according to a signal from the electronic control device 28, in synchronism with the light emissions of the first and second light emitting elements 44a, 44b, and hence successively supplies, to the I/O port (not shown) of the electronic control device 28, an electric signal $SM_R$ due to the red light through a sample-and-hold circuit 56 and an A/D converter 58, and an electric signal $SM_{IR}$ due to the infrared light through a sample-and-hold circuit 60 and an A/D converter 62. When the input electric signals $SM_R$, $SM_{IR}$ are to be output to the A/D converters 58, 62, the sample-and-hold circuits 56, 60 hold the electric signals, respectively, until the operations of converting the electric signals $SM_R$, $SM_{IR}$ which are previously output are completed in the A/D converters 58, 62, respectively.

In the electronic control device 28, the CPU 29 carries out a measuring operation according to programs pre-stored in the ROM 31 by utilizing the storage function of the RAM 33, and outputs a control signal SLV to a drive circuit 64 so as to cause the light emitting elements 44a, 44b to sequentially emit the red light and the infrared light at predetermined frequencies for a predetermined time period. In synchronism with the alternate light emissions by the light emitting elements 44a, 44b, the CPU outputs a switch signal SC to switch over the state of the demultiplexer 54, so that the electric signal $SM_R$ is selectively supplied to the sample-and-hold circuit 56, and the electric signal $SM_{IR}$ to the sample-and-hold circuit 60. The CPU 29 calculates the blood oxygen saturation of the living body, based on the amplitudes of the electric signals $SM_R$, $SM_{IR}$, according to a calculation expression which is previously stored for calculating the blood oxygen saturation.

FIG. 4 is a functional block diagram illustrating the control function of the electronic control device 28 of the blood pressure monitor apparatus 8. Referring to FIG. 4, a blood pressure measuring unit 70 determines the maximal blood pressure value $BP_{SYS}$, the mean blood pressure value $BP_{MEAN}$, the minimal blood pressure value $BP_{DIA}$, and the like, according to an oscillometric method, based on variations of the magnitudes of the pulse wave indicated by the pulse wave signal $SM_1$ which is successively obtained in a slow pressure lowering period in which, after the pressing pressure of the cuff 10 wound around the upper arm of the living body is rapidly increased by a cuff pressure regulating unit 72 to a target pressure value $P_{CM}$ (e.g., a pressure value of about 180 mmHg), the pressure is slowly lowered at a rate of about 3 mmHg/sec.

A pulse wave propagation information calculating unit 74 includes a time-difference calculating unit for, as shown in FIG. 5, successively calculating the time difference (pulse wave propagation time) $DT_{RP}$ from a predetermined portion, for example, the R-wave which is generated in each period of the electrocardiogram successively detected by the electrocardiograph 34, to a predetermined portion, for example, the rising point or lower peak which is generated in each period of the photoplethysmogram successively detected by the probe 38. The pulse wave propagation information calculating unit 74 calculates the propagation velocity $V_M$ (m/sec) of the pulse wave propagated through the artery of the subject, according to Expression 1 which is previously stored, based on the time difference $DT_{RP}$ which is successively calculated by the time-difference calculating unit. In Expression 1, L (m) is the distance from the left ventricle to the portion to which the probe 38 is attached, via the aorta, and $T_{PEP}$ (sec) is the pre-ejection period from the R-wave of the electrocardiogram of to the lower peak of the photoplethysmogram. The distance L and the pre-ejection period $T_{PEP}$ are constants, and experimentally obtained in advance.

$$V_M = L/(DT_{RP} - T_{PEP}) \quad \text{(Exp. 1)}$$

A correspondence relationship determining unit 76 previously determines coefficients $\alpha$ and $\beta$ in a relational expression of the pulse wave propagation time $DT_{RP}$ or the pulse wave propagation velocity $V_M$ indicated by Exp. 2 or Exp. 3 and the maximal blood pressure value $BP_{SYS}$, based on the maximal blood pressure value $BP_{SYS}$ measured by the blood pressure measuring unit 70, and the pulse wave propagation time $DT_{RP}$ or the propagation velocity $V_M$ during each blood pressure measurement period, for example, the average value of the pulse wave propagation time $DT_{RP}$ or the propagation velocity $V_M$ during the period. Alternatively, a relationship of the mean blood pressure value $BP_{MEAN}$ or minimal blood pressure value $BP_{DIA}$ measured by the blood pressure measuring unit 70 in place of the maximal blood pressure value $BP_{SYS}$, and the pulse wave propagation time $DT_{RP}$ or the propagation velocity $V_M$ in the blood pressure measurement period may be obtained. In short, the selection is made depending upon which one of the maximal, mean, and minimal blood pressure values is selected as a monitor blood pressure value (estimated blood pressure value) EBP.

$$EBP = \alpha(DT_{RP}) + \beta \text{ (where } \alpha \text{ is a negative constant and } \beta \text{ is a positive constant)} \quad \text{(Exp. 2)}$$

$$EBP = \alpha(V_M) + \beta \text{ (where } \alpha \text{ is a positive constant and } \beta \text{ is a positive constant)} \quad \text{(Exp. 3)}$$

An estimated blood pressure value determining unit 78 successively determines the estimated blood pressure value EBP based on the actual actual pulse wave propagation time $DT_{RP}$ or propagation velocity $V_M$ which is successively calculated by the pulse wave propagation information obtaining unit 74, according to the correspondence relationship (Exp. 2 and Exp. 3) between the blood pressure value of the living body and the pulse wave propagation time $DT_{RP}$ or the propagation velocity $V_M$ of the living body.

When the estimated blood pressure value determined by the estimated blood pressure value determining unit 78 exceeds a preset determination reference, the blood pressure measurement by the blood pressure measuring unit 70 is executed.

In a related-art blood pressure monitor apparatus in which a pulse wave propagation time measuring unit and a noninvasive blood pressure measuring unit are used together, the blood pressure measurement by the noninvasive blood pressure measuring unit is executed based on that an estimated blood pressure value determined by an estimated blood pressure value determining unit exceeds a preset determination reference (detection threshold). When, in order to enhance the sensitivity to a change of the estimated blood pressure value, the preset determination reference (detection threshold) is set to be small, the noninvasive blood pressure measuring unit is frequently activated, and a large burden is imposed on the patient, and hence it is difficult to set an adequate detection threshold.

SUMMARY

It is therefore an object of the invention to provide a blood pressure monitor apparatus in which a pulse wave propagation time measuring unit and a noninvasive blood pressure measuring unit are used together, and, when an estimated blood pressure value based on the pulse wave propagation time exceeds a preset determination reference, blood pressure measurement by the noninvasive blood pressure measuring unit is executed, and in which a burden on the patient due to frequent activation of the noninvasive blood pressure measuring unit can be reduced.

In order to achieve the object, according to the invention, there is provided a biological information monitor comprising:

a first measuring unit which measures a pulse wave propagation time of a patient;

a second measuring unit which measures a blood pressure of the patient;

a calculating unit which calculates an estimated blood pressure value of the patient based on the pulse wave propagation time of the patient;

a setting unit which sets a threshold; and a determining unit which compares the estimated blood pressure value with the threshold, wherein the second measuring unit is activated to measure the blood pressure of the patient at least one of at time intervals and at a time when an operator operates the second measuring unit, and the second measuring unit is activated to measure the blood pressure of the patient by the determining unit based on the comparison result.

The threshold may include first and second upper limits which are different from each other and first and second lower limits which are different from each other.

The first upper limit may be upper than the second upper limit, and the first lower limit may be lower than the second lower limit. When the estimated blood pressure value exceeds the second upper limit or falls below the second lower limit, the second measuring unit may be activated to measure the blood pressure of the patient.

The first upper limit may be upper than the second upper limit, and the first lower limit may be lower than the second lower limit. In a case where a time period when the estimated blood pressure value exceeds the second upper limit or falls below the second lower limit is shorter than a predetermined time period, the second measuring unit is not activated.

The first upper limit may be upper than the second upper limit. When the estimated blood pressure value exceeds the first upper limit, the second measuring unit may be activated to measure the blood pressure of the patient. After the estimated blood pressure value exceeds the first upper limit, the second measuring unit is not activated unless the estimated blood pressure value falls below the second upper limit.

The first lower limit may be lower than the second lower limit. When the estimated blood pressure value falls below the first lower limit, the second measuring unit may be activated to measure the blood pressure of the patient. After the estimated blood pressure value falls below the first lower limit, the second measuring unit is not activated unless the estimated blood pressure value exceeds the second lower limit.

The estimated blood pressure value may be calculated by an expression of $EBP=\alpha \times PWTT+\beta$, where EBP is the estimated blood pressure value, PWTT is the pulse wave propagation time, and $\alpha$ and $\beta$ are constants. The $\alpha$ and $\beta$ may be updated so that the estimated blood pressure value is equal to a value of the blood pressure of the patient measured by activating the second measuring unit at least one of at time intervals and at the time when the operator operates the second measuring unit.

During a time period when the second measuring unit is activated to measure the blood pressure of the patient at least one of at time intervals and at the time when the operator operates the second measuring unit, calculation of the estimated blood pressure value may be halted.

The biological information monitor may further include a display portion on which the threshold and the estimated blood pressure value are simultaneously displayed.

DETAILED DESCRIPTION OF EMBODIMENTS

The configuration of the invention will be described with reference to FIG. 1.

Figure 1:
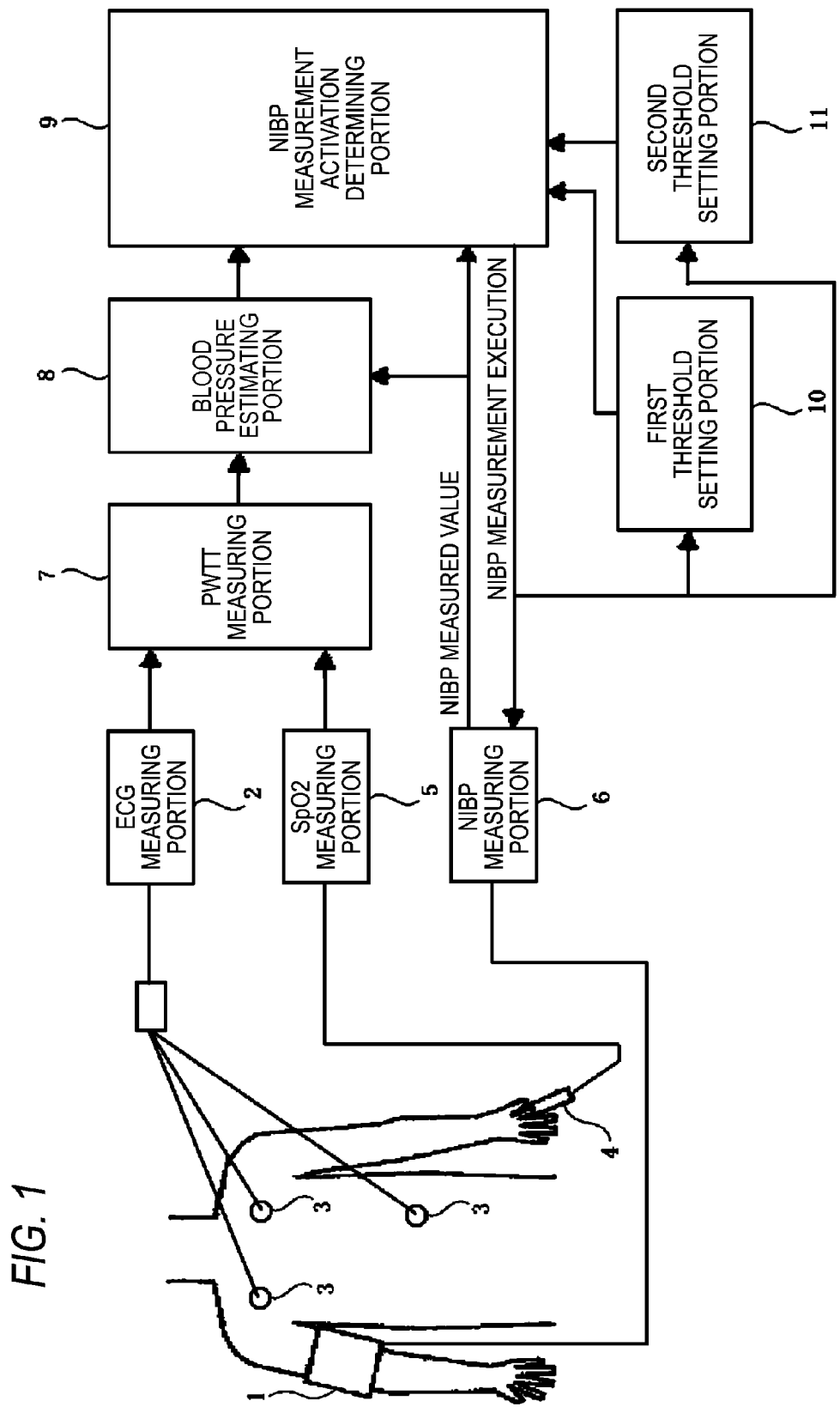
FIG. 1 is a block diagram illustrating the configuration of a blood pressure monitor apparatus of the invention.

Referring to FIG. 1, a biological information monitor of the invention includes as measuring portions: an electrocardiogram (ECG) measuring portion 2 which detects an electrocardiogram indicative of the action potential of the cardiac muscle through a plurality of electrodes 3 which are applied to predetermined portions of the patient; a pulse wave (SpO2) measuring portion 5 which detects a pulse wave propagated to a peripheral artery including capillaries, by means of a photoplethysmographic detecting probe 4 which is attached to a finger or the like of the patient; and a noninvasive blood pressure (NIBP) measuring portion 6 which measures a blood pressure of the patient by means of a cuff 1 wound around an upper arm of the patient.

The biological information monitor of the invention shown in FIG. 1 further includes a pulse wave propagation time (PWTT) measuring portion 7 that successively calculates the time difference (pulse wave propagation time) (PWTT) from a predetermined portion, for example, the R-wave which is generated in each period of the electrocardiogram which is successively detected by the ECG measuring portion 2 in response to measurement signals of the ECG measuring portion and the SpO2 measuring portion 5, to a predetermined portion, for example, the rising point or lower peak which is generated in each period of the photoplethysmogram which is successively detected by the probe 4.

A blood pressure estimating portion 8 shown in FIG. 1 each time calculates an estimated blood pressure value (EBP) of the patient from the pulse wave propagation time PWTT of the patient which is measured by the PWTT measuring portion 7, by a conversion expression of $EBP=\alpha \times PWTT+\beta$ (where $\alpha$ and $\beta$ are coefficients).

An NIBP measurement activation determining portion 9 shown in FIG. 1 compares the estimated blood pressure value of the patient which is obtained as a result of the conversion in the blood pressure estimating portion 8, with threshold values, which are set by a first threshold setting portion 10 and a second threshold setting portion 11, to activate the NIBP measuring portion 6 based on the comparison result. In a case that upper and lower limit alarm set values in monitoring of the blood pressure of the patient are set as the first threshold values in the biological information monitor, a new process and a member for setting the alarm in monitoring of the blood pressure are not required. However, the first threshold values are not restricted to the alarm set values.

In the biological information monitor of the invention shown in FIG. 1, $\alpha$ and $\beta$ in the conversion expression of EBP=$\alpha \times$PWTT+$\beta$ are updated so that the above described estimated blood pressure value is equal to an actual blood pressure value which is measured by at least one of measurement executed at predetermined time intervals by the NIBP measuring portion 6 and measurement by the NIBP measuring portion 6 which is operated by the operator, whereby the accuracy of the estimated blood pressure value can be further enhanced.

In the biological information monitor of the invention shown in FIG. 1, during measurement by the NIBP measuring portion 6, there is a possibility that a burden is imposed on the patient to affect the calculation of the above described estimated blood pressure value. During measurement executed at predetermined time intervals by the NIBP measuring portion 6 or measurement by the NIBP measuring portion 6 which is operated by the operator, therefore, the calculation of the above described estimated blood pressure value is halted, whereby the accuracy of the estimated blood pressure value can be further enhanced.

Next, relationships between first thresholds a1, b1 which are set by the first threshold setting portion 10 and second thresholds a2, b2 which are set by the second threshold setting portion 11, and the activation of the NIBP measuring portion 6 due to comparison with the estimated blood pressure value will be described with reference to FIGS. 2A to 2C.

Figure 2A:
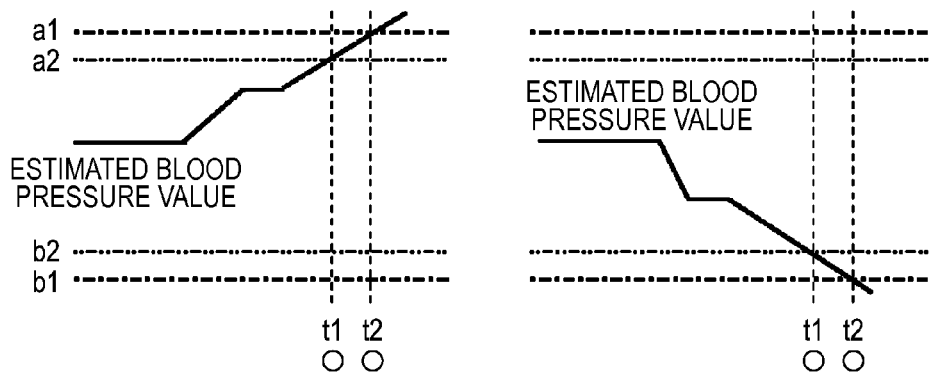
FIGS. 2A to 2C are views showing relationships between first thresholds a1, b1 which are set by a first threshold setting portion and second thresholds a2, b2 which are set by a second threshold setting portion, and activation of an NIBP measuring portion due to comparison with an estimated blood pressure value.

FIG. 2A is a view showing relationships between first thresholds a1, b1 and second thresholds a2, b2, and an estimated blood pressure value in Set example 1.

The first thresholds a1, b1 in FIG. 2A indicate blood pressure values corresponding to the related-art determination reference. In the related art, when the estimated blood pressure value determined by the estimated blood pressure value determining unit 78 exceeds (falls below) the determination reference, the blood pressure measurement by the blood pressure measuring unit 70 is executed. The first threshold a1 corresponds to an upper limit, and the first threshold b1 corresponds to a lower limit.

In FIG. 2A, the second thresholds a2, b2 are set inside the first thresholds a1, b1.

In the left graph of FIG. 2A, the estimated blood pressure value is usually changed inside the second thresholds a2, b2.

At both timings t1 and t2 when the estimated blood pressure value exceeds the second threshold a2 and the first threshold a1 which are upper limits, the measurement of the blood pressure of the patient by the NIBP measuring portion 6 is executed.

During a time shown in the left graph of FIG. 2A, the blood pressure of the patient is measured by at least one of measurement executed at predetermined time intervals by the NIBP measuring portion 6 and measurement by the NIBP measuring portion 6 which is operated by the operator.

Also in the right graph of FIG. 2A, similarly, the estimated blood pressure value is usually changed inside the second thresholds a2, b2.

At both timings t1 and t2 when the estimated blood pressure value falls below the second threshold b2 and the first threshold b1 which are lower limits, the measurement of the blood pressure of the patient by the NIBP measuring portion 6 is executed.

Also during a time shown in the right graph of FIG. 2A, similarly, the blood pressure of the patient is measured by at least one of measurement executed at predetermined time intervals by the NIBP measuring portion 6 and measurement by the NIBP measuring portion 6 which is operated by the operator.

In FIG. 2A, as described above, the first thresholds are set to the upper and lower limit alarm set values in monitoring of the blood pressure of the patient, and the second thresholds are set inside the upper and lower limit alarm set values. Therefore, the blood pressure of the patient is measured by at least one of measurement executed at predetermined time intervals by the NIBP measuring portion 6 and measurement by the NIBP measuring portion 6 which is operated by the operator, and, at the both timings when the estimated blood pressure value exceeds the first and second thresholds which are the upper limits and falls below the first and second thresholds which are lower limits, the measurement of the blood pressure of the patient by the NIBP measuring portion 6 is executed. Therefore, it is possible to cope with a sudden change of the blood pressure of the patient.

Further, in the case where a time period when the estimated blood pressure value exceeds the second threshold a2 or falls below the second threshold b2 is shorter than a predetermined time period, the measurement of the blood pressure of the patient by the NIBP measuring portion 6 may be halted.

Figure 2B:
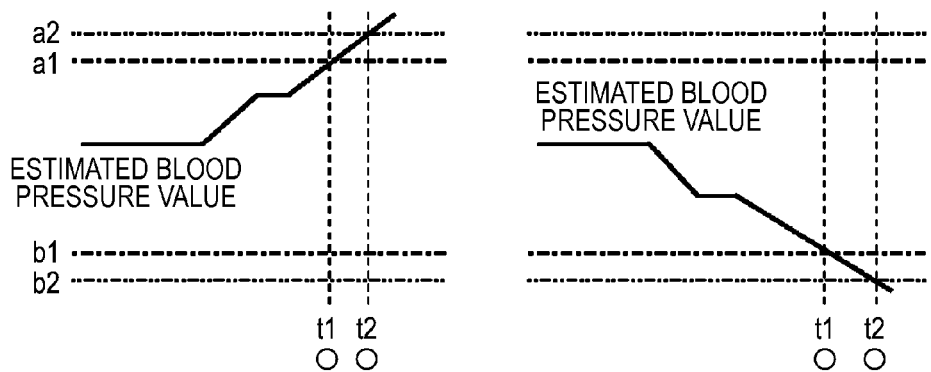

FIG. 2B is a view showing relationships between first thresholds a1, b1 and second thresholds a2, b2, and an estimated blood pressure value in Set example 2.

The first thresholds a1, b1 in FIG. 2B indicate blood pressure values corresponding to the related-art determination reference. The first threshold a1 corresponds to an upper limit, and the first threshold b1 corresponds to a lower limit.

In FIG. 2B, the second thresholds a2, b2 are set outside the first thresholds a1, b1.

In the left graph of FIG. 2B, the estimated blood pressure value is usually changed inside the first thresholds a1, b1.

At both timings t1 and t2 when the estimated blood pressure value exceeds the first threshold a1 and the second threshold a2 which are upper limits, the measurement of the blood pressure of the patient by the NIBP measuring portion 6 is executed.

During a time in the left graph of FIG. 2B, the blood pressure of the patient is measured by at least one of measurement executed at predetermined time intervals by the NIBP measuring portion 6 and measurement by the NIBP measuring portion 6 which is operated by the operator.

Also in the right graph of FIG. 2B, similarly, the estimated blood pressure value is usually changed inside the first thresholds a1, b1.

At both timings t1 and t2 when the estimated blood pressure value falls below the first threshold b1 and the second threshold b2, the measurement of the blood pressure of the patient by the NIBP measuring portion 6 is executed.

Also during a time shown in the right graph of FIG. 2B, similarly, the blood pressure of the patient is measured by at least one of measurement executed at predetermined time intervals by the NIBP measuring portion 6 and measurement by the NIBP measuring portion 6 which is operated by the operator.

In Set example 2 of FIG. 2B, as compared with Set example 1 of FIG. 2A, the number of measurements of the blood pressure of the patient by the NIBP measuring portion 6 may be reduced, so that the burden on the patient may be reduced.

Figure 2C:
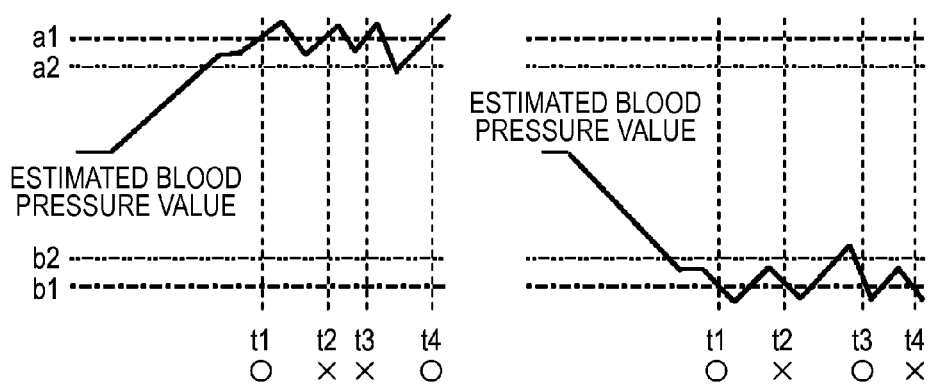
Figure 3:
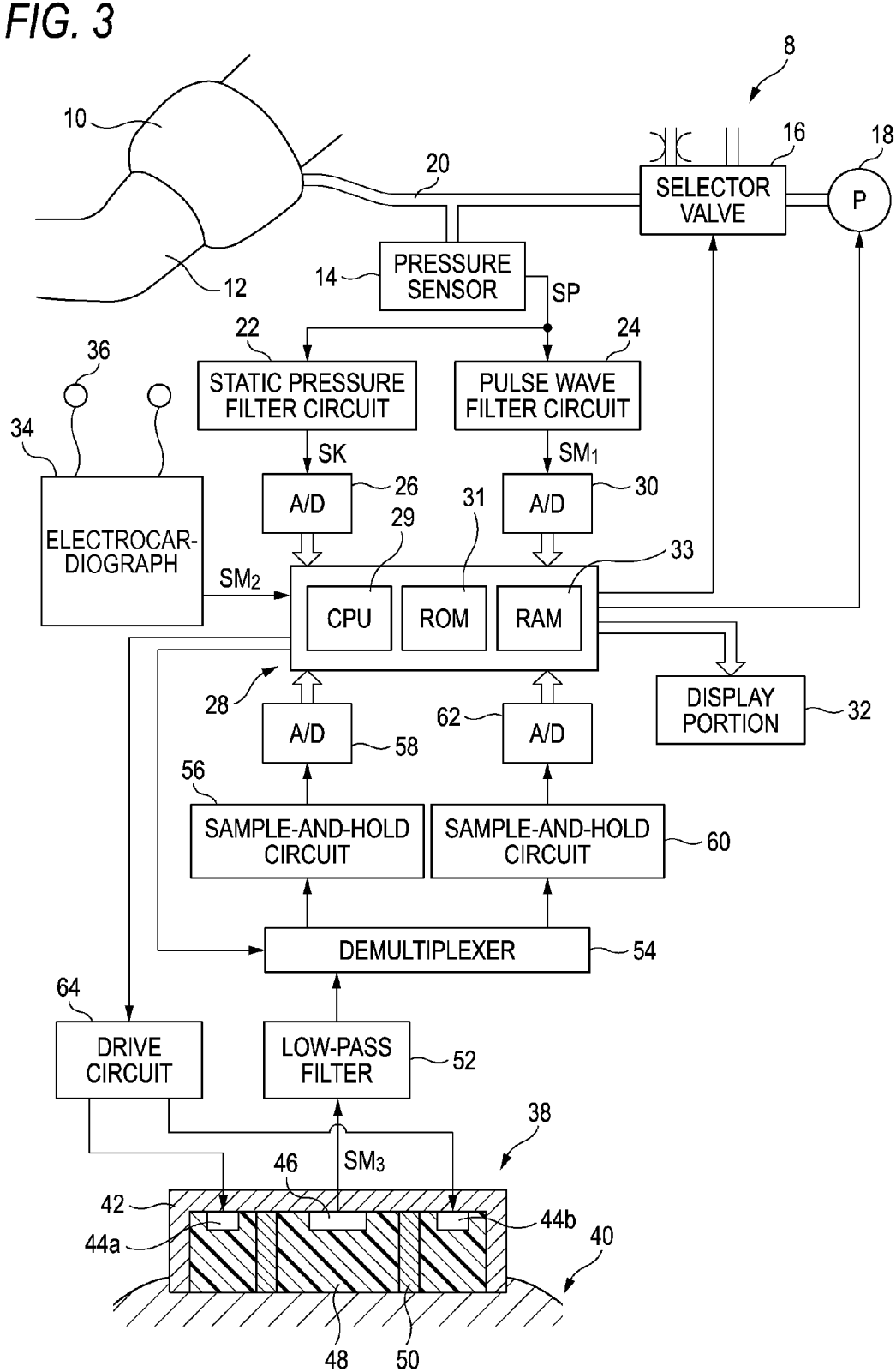
FIG. 3 is a block diagram illustrating the configuration of a related-art blood pressure monitor apparatus.
Figure 4:
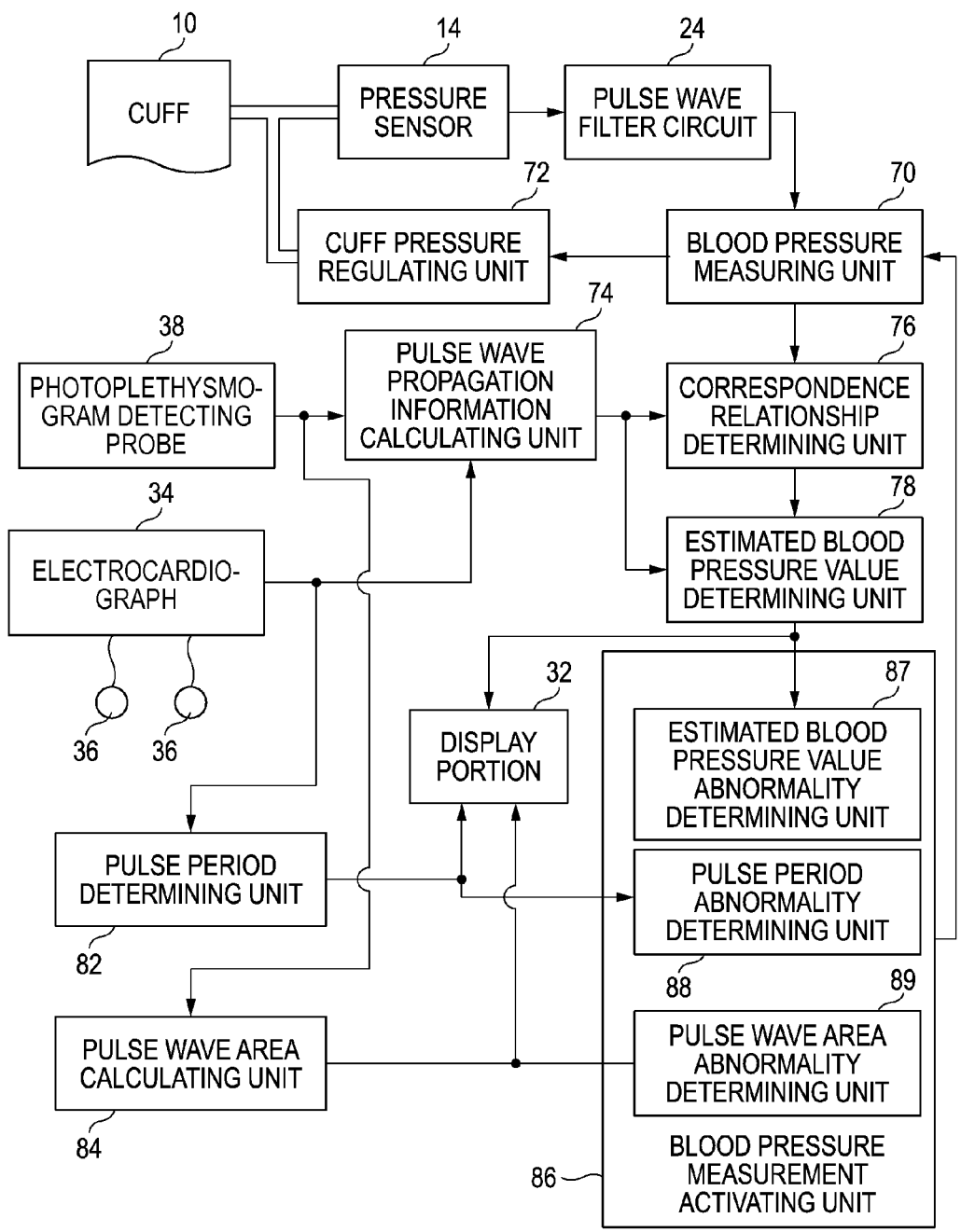
FIG. 4 is a functional block diagram illustrating the control function of an electronic control device in the related-art blood pressure monitor apparatus.
Figure 5:
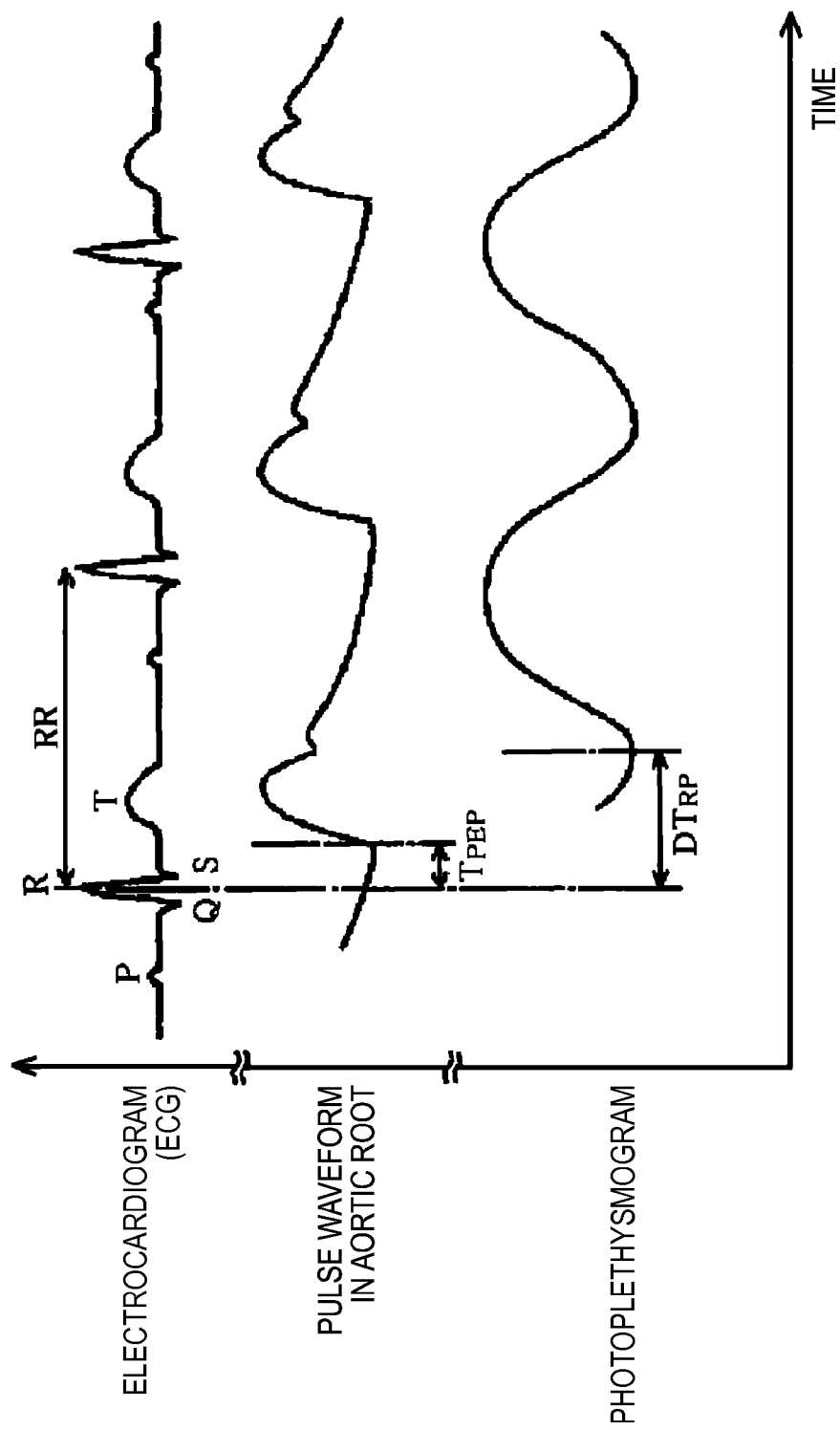
FIG. 5 is a view showing relationships of a time difference (pulse wave propagation time) from a predetermined portion, for example, the R-wave which is generated in each period of the electrocardiogram successively detected by an electrocardiograph, to a predetermined portion, for example, a rising point or lower peak which is generated in each period of a photoplethysmogram successively detected by a probe.

FIG. 2C is a view showing relationships between first thresholds a1, b1 and second thresholds a2, b2, and an estimated blood pressure value in Set example 3.

The first thresholds a1, b1 in FIG. 2C indicate blood pressure values corresponding to the related-art determination reference. The first threshold a1 corresponds to an upper limit, and the first threshold b1 corresponds to a lower limit.

In FIG. 2C, the second thresholds a2, b2 are set inside the first thresholds a1, b1.

In the left graph of FIG. 2C, the estimated blood pressure value is usually changed inside the second thresholds a2, b2.

At the timing when the estimated blood pressure value exceeds the second threshold a2, the measurement of the blood pressure of the patient by the NIBP measuring portion 6 is not executed.

In the case where, after the estimated blood pressure value exceeds the second threshold a2, the estimated blood pressure value exceeds the first threshold a1 (at a timing t1), however, the measurement of the blood pressure of the patient by the NIBP measuring portion 6 is executed.

After the blood pressure of the patient is measured at the timing t1 by the NIBP measuring portion 6, even when the estimated blood pressure value again exceeds the first threshold a1 at timings t2 and t3, the measurement of the blood pressure of the patient by the NIBP measuring portion 6 is not executed unless the estimated blood pressure value falls below the second threshold a2.

After the blood pressure of the patient is measured at the timing t1 by the NIBP measuring portion 6, when the estimated blood pressure value falls below the second threshold a2, however, the measurement of the blood pressure of the patient by the NIBP measuring portion 6 is executed at a timing t4 when the estimated blood pressure value again exceeds the first threshold a1.

Also during a time shown in the left graph of FIG. 2C, the blood pressure of the patient is measured by at least one of measurement executed at predetermined time intervals by the NIBP measuring portion 6 and measurement by the NIBP measuring portion 6 which is operated by the operator.

In the right graph of FIG. 2C, the estimated blood pressure value is usually changed inside the second thresholds a2, b2.

At a timing when the estimated blood pressure value falls below the second threshold b2, the measurement of the blood pressure of the patient by the NIBP measuring portion 6 is not executed.

In the case where, after the estimated blood pressure value falls below the second threshold b2, the estimated blood pressure value falls below the first threshold b1 (at a timing t1), however, the measurement of the blood pressure of the patient by the NIBP measuring portion 6 is executed.

After the blood pressure of the patient is measured at the timing t1 by the NIBP measuring portion 6, even when the estimated blood pressure value again falls below the first threshold b1 at a timing t2, the measurement of the blood pressure of the patient by the NIBP measuring portion 6 is not executed unless the estimated blood pressure value exceeds the second threshold b2.

After the blood pressure of the patient is measured at the timing t1 by the NIBP measuring portion 6, when the estimated blood pressure value exceeds the second threshold b2, however, the measurement of the blood pressure of the patient by the NIBP measuring portion 6 is executed at a timing t3 when the estimated blood pressure value again falls below the first threshold b1.

After the blood pressure of the patient is measured at the timing t3 by the NIBP measuring portion 6, even when the estimated blood pressure value again falls below the first threshold b1 at a timing t4, the measurement of the blood pressure of the patient by the NIBP measuring portion 6 is not executed unless the estimated blood pressure value exceeds the second threshold b2.

Also during a time shown in the right graph of FIG. 2C, the blood pressure of the patient is measured by at least one of measurement executed at predetermined time intervals by the NIBP measuring portion 6 and measurement by the NIBP measuring portion 6 which is operated by the operator.

In Set example 3 of FIG. 2C, as compared with Set example 1 of FIG. 2A and Set example 2 of FIG. 2B, frequent execution of the measurement of the blood pressure of the patient by the NIBP measuring portion 6 is reduced, so that the burden on the patient may be reduced.

In any of the cases of FIGS. 2A, 2B, and 2C, in the case where a predetermined time period has not elapsed from the timing when the measurement of the blood pressure of the patient by the NIBP measuring portion 6 (including both of the measurement executed when the estimated blood pressure value exceeds (falls below) the threshold, and the measurement executed at predetermined time intervals or operated by the operator) is executed, the measurement of the blood pressure of the patient by the NIBP measuring portion 6 may be omitted, so that the burden on the patient may be further reduced.

Figure 6:
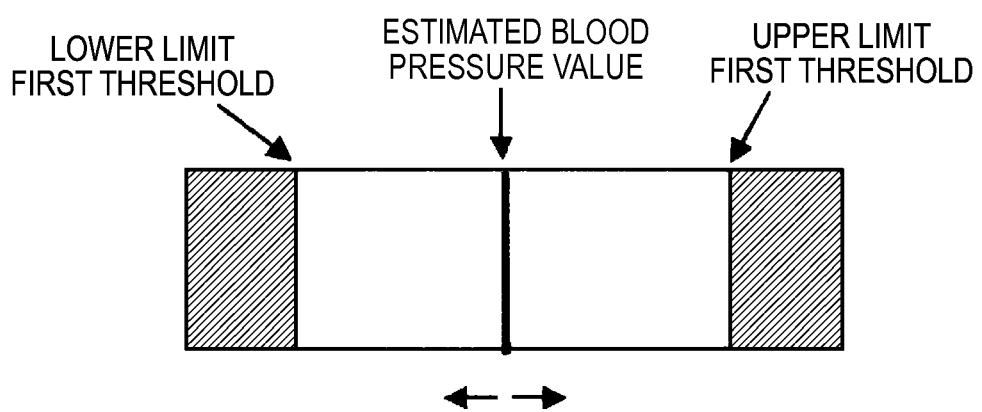
FIG. 6 is a view showing a simultaneous display of first thresholds and an estimated blood pressure value on a displaying portion of a biological information monitor.

In order to check the start of the blood pressure measurement, at least one of the first and second thresholds are displayed together with the estimated blood pressure value on a displaying portion of the biological information monitor. In FIG. 6, the first thresholds and the estimated blood pressure value are simultaneously displayed on the displaying portion of the biological information monitor.

According to an aspect of the invention, a burden on the patient due to frequent activation of the noninvasive blood pressure measuring unit can be reduced.

What is claimed is:
1. A biological information monitor comprising:
a first measuring unit which measures a pulse wave propagation time of a patient;
a second measuring unit which measures a blood pressure of the patient;
a calculating unit which calculates an estimated blood pressure value of the patient based on the pulse wave propagation time of the patient;
a setting unit which sets a threshold; and
a determining unit which compares the estimated blood pressure value with a first upper limit, a second upper limit, a first lower limit, and a second lower limit,
wherein when the estimated blood pressure exceeds the second upper limit, the second measuring unit is not activated,
wherein when the estimated blood pressure exceeds the first upper limit, the second measuring unit is activated to measure the blood pressure of the patient, and after the estimated blood pressure value exceeds the first upper limit, the second measuring unit is not activated unless the estimated blood pressure value falls below the second upper limit and then exceeds the first upper limit again,
wherein the first and second upper limits are different from each other and the first upper limit is greater than the second upper limit;

wherein when the estimated blood pressure falls below the second lower limit, the second measuring unit is not activated, wherein when the estimated blood pressure falls below the first lower limit, the second measuring unit is activated to measure the blood pressure of the patient and after the estimated blood pressure value falls below the first lower limit, the second measuring unit is not activated unless the estimated blood pressure value exceeds the second lower limit and then falls below the first lower limit again, and wherein the first and second lower limits are different from each other and the first lower limit is less than the second lower limit.

2. The biological information monitor according to claim 1, wherein the estimated blood pressure value is calculated by an expression of $EBP = \alpha \times PWTT + \beta$, where EBP is the estimated blood pressure value, PWTT is the pulse wave propagation time, and $\alpha$ and $\beta$ are constants, and the $\alpha$ and $\beta$ are updated so that the estimated blood pressure value is equal to a value of the blood pressure of the patient measured by activating the second measuring unit at least one of at time intervals and at a time when the operator operates the second measuring unit.

3. The biological information monitor according to claim 1, wherein during a time period when the second measuring unit is activated to measure the blood pressure of the patient at least one of at time intervals and at a time when the operator operates the second measuring unit, calculation of the estimated blood pressure value is halted.

4. The biological information monitor according to claim 1, further comprising:
 a display portion on which at least one of the first upper limit, the first lower limit, the second upper limit, and the second lower limit and the estimated blood pressure value are simultaneously displayed.

5. The biological information monitor according to claim 1, wherein the determining unit determines whether a time period when the estimated blood pressure value exceeds the second upper limit or falls below the second lower limit is shorter than a predetermined time period, the determining unit withholds activation of the second measuring unit when the time period is shorter than the predetermined time.

* * * * *